United States Patent [19]
Komesaroff

[11] Patent Number: 5,816,240
[45] Date of Patent: Oct. 6, 1998

[54] SPACER

[75] Inventor: David Komesaroff, Melbourne, Australia

[73] Assignee: Techbase Pty. Ltd., Melbourne, Australia

[21] Appl. No.: 816,587

[22] Filed: Mar. 13, 1997

[30] Foreign Application Priority Data

Jul. 14, 1995 [AU] Australia .................................. PN4173

[51] Int. Cl.$^6$ .................................................. A61M 15/00
[52] U.S. Cl. ............................... 128/200.23; 128/200.14; 128/207.12
[58] Field of Search ......................... 128/200.23, 200.14, 128/203.12, 203.15, 203.29, 203.11, 202.28, 202.29, 207.12, 207.16, 205.24

[56] References Cited

U.S. PATENT DOCUMENTS

| | | | |
|---|---|---|---|
| 3,262,446 | 7/1966 | Stoner . | |
| 4,174,712 | 11/1979 | Moren et al. . | |
| 4,470,412 | 9/1984 | Nowacki et al. .................. | 128/200.23 |
| 4,774,941 | 10/1988 | Cook . | |
| 4,834,085 | 5/1989 | Webster, II ........................ | 128/202.29 |
| 4,852,561 | 8/1989 | Sperry ................................ | 128/200.23 |
| 4,940,051 | 7/1990 | Lankinen ........................... | 128/200.23 |
| 5,012,804 | 5/1991 | Foley et al. ........................ | 128/203.29 |
| 5,074,294 | 12/1991 | Chiesi ................................. | 128/200.14 |
| 5,099,833 | 3/1992 | Michaels . | |
| 5,127,397 | 7/1992 | Kohnke .............................. | 128/203.11 |
| 5,163,424 | 11/1992 | Kohnke .............................. | 128/203.11 |
| 5,178,138 | 1/1993 | Walstrom et al. ................. | 128/200.14 |
| 5,231,982 | 8/1993 | Harrison et al. ................... | 128/207.12 |
| 5,427,089 | 6/1995 | Kraemer ............................ | 128/203.29 |
| 5,497,765 | 3/1996 | Praud et al. . | |
| 5,598,836 | 2/1997 | Larson et al. ...................... | 128/200.23 |

FOREIGN PATENT DOCUMENTS

| | | | |
|---|---|---|---|
| 88/02267 | 4/1988 | WIPO ................................ | 128/200.23 |

Primary Examiner—Mark O. Polutta
Assistant Examiner—V. Srivastava
Attorney, Agent, or Firm—Bose McKinney & Evans

[57] ABSTRACT

An improved spacer (10) for use in administering an aerosol medication to a patient includes a spacer body member (30) having a cylindrical wall (50) defining a generally hollow chamber (56), and a patient delivery member (20) in fluid communication with the chamber (56), through which medication can be delivered to the patient and a medication inlet (40). The patient delivery member (20) includes a mouthpiece (21) through which the patient can inspire medication from the chamber (56) and expire gases. An inspiratory valve (32) is coupled between the mouthpiece (21) and the chamber (56). The inspiratory valve (32) is configured for opening on inspiration by the patient, and closing upon expiration by the patient. An expiratory valve (23) is coupled between the mouthpiece (21) and an expiratory outlet (24) external of the chamber (56). The expiratory valve (23) is configured for opening upon expiration by the patient, and closing upon inspiration by the patient. The medication inlet (40) is in fluid communication with the chamber (56) through which medication can be introduced to the chamber (56). The medication inlet (40) includes a retaining means (44 or 46) for retaining a medication delivery device on a medication inlet housing member (41). The mouthpiece (21) is configured to enable the fitting of standard adult and child face masks and standard connectors with either male or female international taper fittings. The medication inlet housing (41) can include at least one additional medication inlet (43) that allows the simultaneous administration of other gases such as oxygen and/or aerosol medication. A modified spacer (210) in which the inspiratory and expiratory valves are absent, is used for introducing aerosol medication into a breathing circuit. The expiratory valve is replaced by closure disk (23b), and retaining means 46 is used in lieu of retaining spring 44.

39 Claims, 7 Drawing Sheets

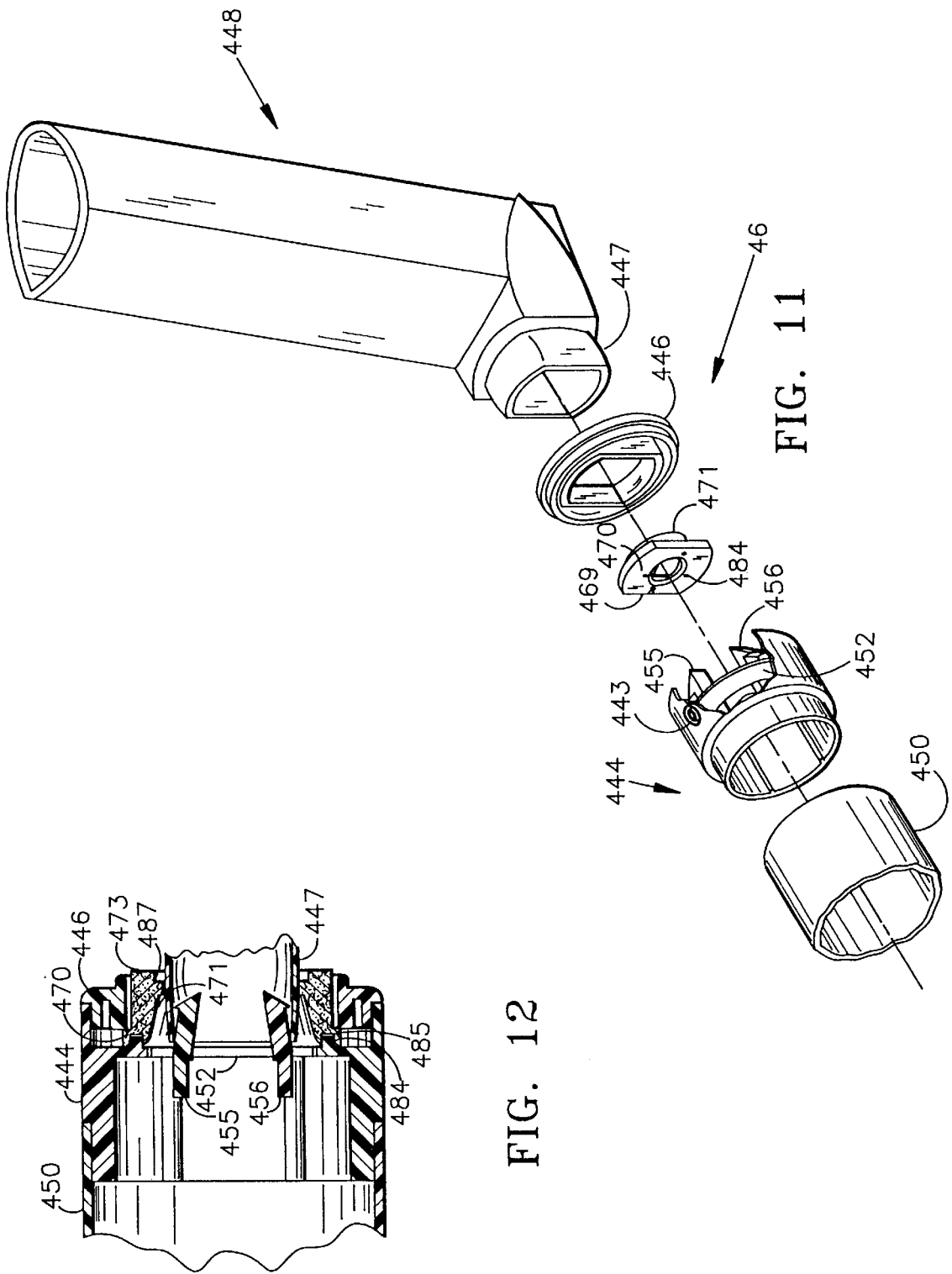

SPACER

This is a continuation-in-part of PCT application no. PCT/IB96/01028 filed on 12 Jul. 1996, which claims priority to Australian Provisional Patent Application No. PN4173 filed 14 Jul. 1995.

TECHNICAL FIELD OF THE INVENTION

The invention relates to an improved spacer for administration of aerosol medication and in particular asthma aerosol medication.

BACKGROUND OF THE INVENTION

Medication for breathing ailments and difficulties, such as asthma are most often administered using a medication delivery means such as an aerosol pressurized cartridge mechanism which is inserted directly into the mouth. However, due to the nature of the aerosol system, the medication is propelled out of the pressurized container in a short dosage burst. Because the patients who need such medication are having difficulty in breathing, they are unable to inhale quickly and strongly enough to capture the full dose of medication.

Spacers have been developed in order to allow people to have more time to inhale the full dosage and to minimize "throat impaction," wherein the medication impacts the lining of the throat, rather than reaching the lungs. Essentially, spacers comprise a medication inlet, a breathing inlet and a chamber in between. The medication inlet of the spacer usually accommodates the outlet of the medication inhaler, which is known as an "MDI" (metered dose inhaler). The breathing inlet allows the patient to breathe in the medication from the aerosol in the chamber over a number of breaths. In use, an MDI containing the pharmaceutical type medication is attached to the medication inlet of the spacer, a dosage is administered to the chamber, which captures the medication, and the patient then breathes the medication in a more efficient manner.

One of the major problems with existing spacers is that while adults and older children are generally able to use them, neonates, infants and small children are generally not able or willing to master the technique of breathing in the medication without extreme difficulty. The mouthpieces of existing spacers are designed for adults and older children and do not adequately meet the requirements of neonates, infants and small children who therefore require the assistance of user friendly small masks to receive the medication.

Another problem with known spacers is that they have been very specific and simplistic in design. In particular they can only be used in relation to personal inhalers and have not been easily adapted to professional or hospital use. Furthermore, known spacers have only allowed the introduction of the medication alone and not in conjunction with other necessary medication gases, such as oxygen, which is often necessary, particularly during emergencies in the home or hospital usage, where oxygen may be required to be administered at the same time as the aerosol medication.

Another major problem with existing spacers is that it is generally quite difficult, and in some cases very difficult, for the patient to breathe the medication in and breathe out because of the inherent resistance of the spacer. This becomes more of a problem when the patient is critically ill and very weak and is already having extreme difficulties in breathing.

Thus, it is an object of the present invention to attempt to overcome the problems of the prior art and provide an improved spacer.

SUMMARY OF THE PRESENT INVENTION

In accordance with the present invention, a spacer is provided for the administration of an aerosol medication to a patient. The spacer comprises a spacer body member defining a generally hollow chamber, and a patient delivery means in fluid communication with the chamber, through which medication can be delivered to the patient and a medication inlet. The patient delivery means includes a mouthpiece means through which the patient can inspire medication from the chamber and expire gases to the atmosphere. An inspiratory valve means is coupled between the mouthpiece and the chamber. The inspiratory valve means is configured for opening on inspiration by the patient, and closing upon expiration by the user. An expiratory valve means is coupled between the mouthpiece and an expiratory outlet external of the chamber. The expiratory valve means is configured for opening upon expiration by the patient, and closing upon inspiration by the patient.

A medication inlet means is in fluid communication with the chamber through which medication can be introduced to the chamber. The medication inlet means includes a retaining means for retaining a medication delivery means in the medication inlet means.

One feature of the present invention is that it provides a spacer for the administration of aerosol medication including a patient inlet/outlet means which includes an integral mouthpiece that enables the fitting of standard adult and child face masks and standard connectors with either male or female international taper fittings. The integral mouthpiece preferably includes both means to retain an adult mask and fittings and means to retain a child mask and fittings.

A major feature of the present invention is that it employs a unique retaining means that is captured by, and cannot be dislodged from the spacer body, and has the advantage of being designed to accept and securely hold all sizes of MDIs. Additionally, the retaining means is preferably made from a heat resistant material that permits heat sterilization of the device.

Advantageously, the present invention provides a spacer that can be easily and effectively be used in adults, neonates, infants and children in either domestic, professional or hospital use.

Preferably, the present invention provides a spacer for the administration of aerosol medication including a patient inlet/outlet means, a chamber means and a medication inlet means wherein the medication inlet means has at least one additional (second) inlet means which allows the simultaneous administration of other medications such as oxygen or aerosol medication. The second inlet provides the user with a great deal of flexibility when using the device. For example, oxygen can be introduced into the second inlet while a metered dose inhaler delivery tube is inserted in the primary medication inlet. In this mode, the applicant has found that an effective oxygen concentration of about 35% can be delivered to the patient when oxygen is delivered at flow rates of about 3 liters per minute. Alternately, the cartridge from the MDI can be inserted into the second medication inlet, and an oxygen tube connected to the first medication inlet (via a connector). The applicant has found that this arrangement can provide the patient with a 90% oxygen concentration when oxygen is delivered at flow rates of about 8 liters per minute.

The present invention also provides a spacer for the administration of aerosol medication including a patient inlet/outlet means, a chamber means and a medication inlet means wherein the patient inlet/outlet means includes an inspiratory and an expiratory valve means which enables easier inhalation and exhalation by the user.

Further, the invention can provide a spacer that can be used for domestic use, by professional medical persons and also during resuscitation, anesthesia or intensive care because of its improved characteristics of easier inhalation and flexibility in use. In particular, the ability to simultaneously administer aerosol medication and oxygen (or other gases) allow the use of the spacer even with critically ill patients including those who have recurring asthma.

BRIEF DESCRIPTION OF THE DRAWINGS

FIG. 11 is an exploded view of an alternate embodiment medication inlet means and retaining means; and FIG. 12 is a side, sectional view of the alternate embodiment medication inlet means of FIG. 11, installed in a medical spacer of the present invention.

DETAILED DESCRIPTION

Figure 1:
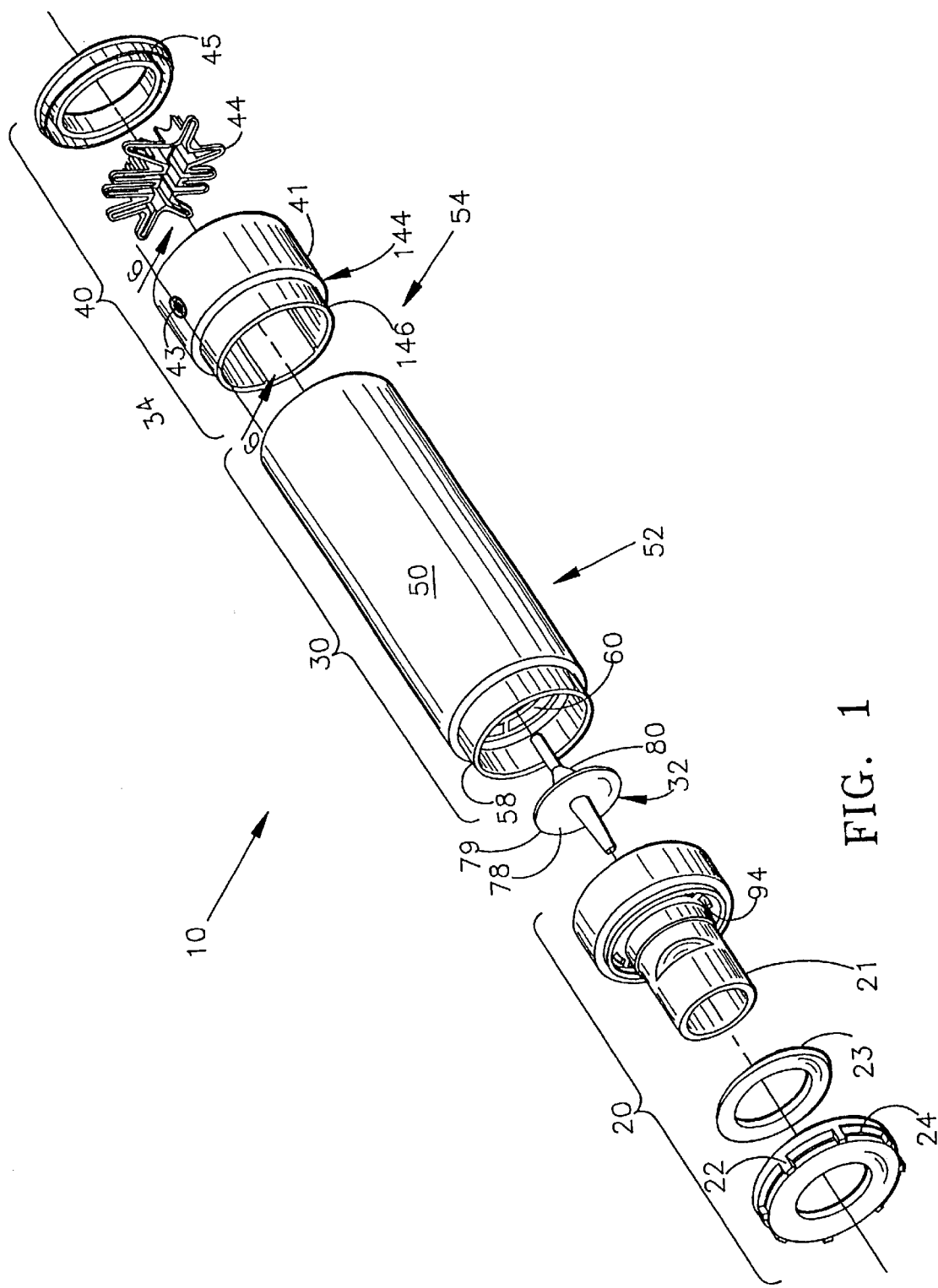
FIG. 1 illustrates an embodiment of the spacer of the present invention.

A spacer 10 of the present invention is used for the administration of an aerosol medication (not shown) to a patient (not shown). The spacer 10 includes a generally cylindrical spacer body member 30 that defines a generally hollow interior chamber 56. A patient delivery means 20 is connected to the first end of the spacer body 30, and is in fluid communication with the interior chamber 56 of the spacer body 30. The patient delivery means 20 is provided for delivering the medication that is within the chamber 56 to the patient.

Figure 5A:
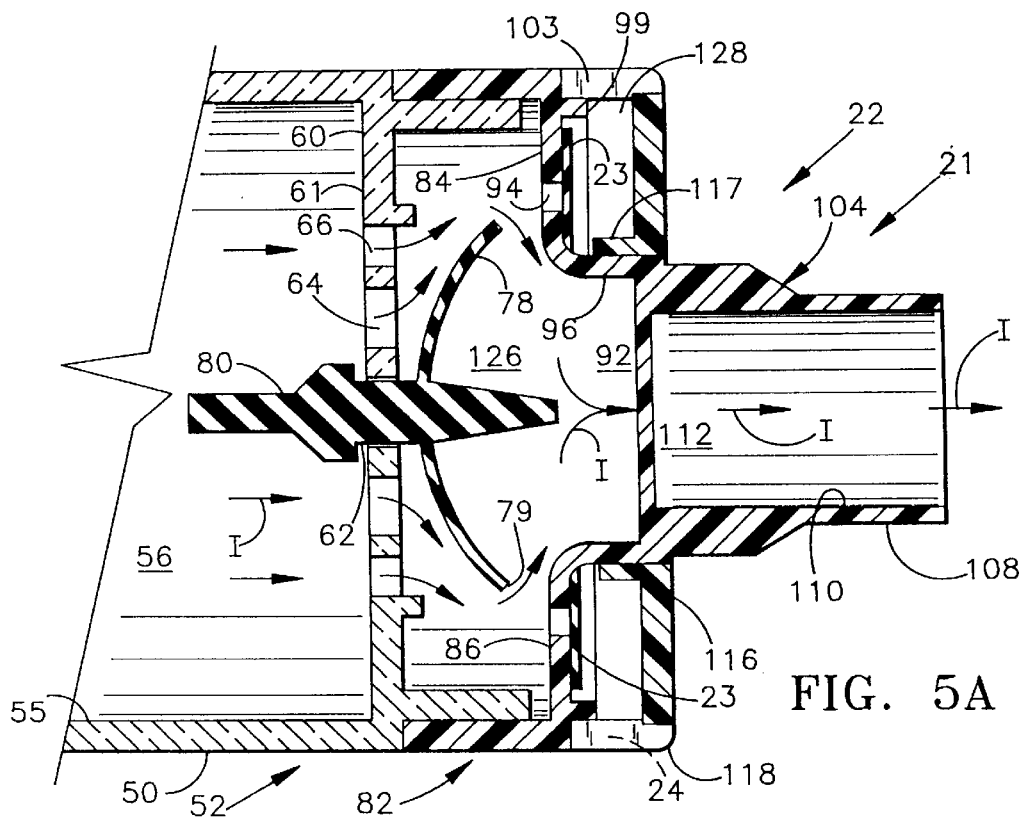
FIG. 5A is an enlarged, sectional view of the patient delivery means of the present invention, showing the valves thereof in their inspiratory position.
Figure 5B:
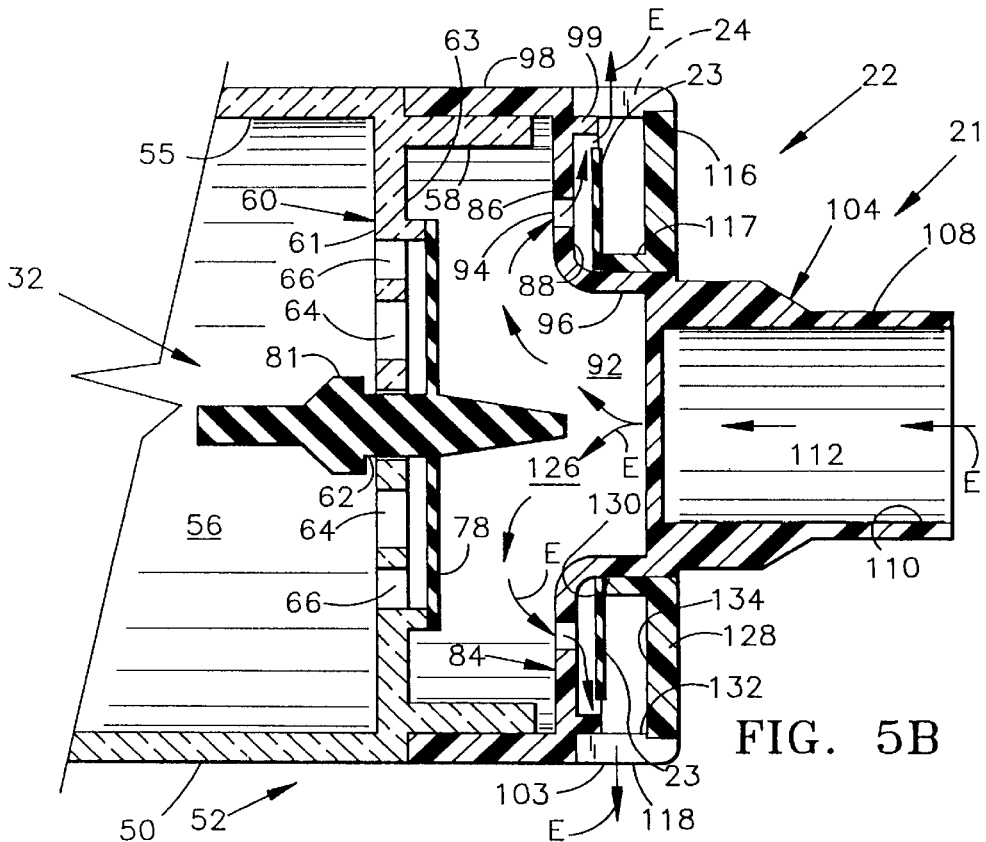
FIG. 5B is an enlarged, sectional view of the patient delivery means of the present invention, showing the valves in their expiratory position.
Figure 6:
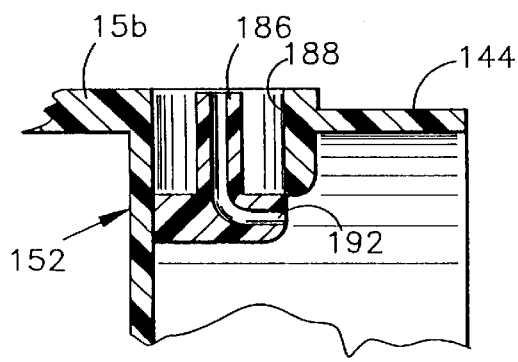
FIG. 6 is an enlarged, sectional view of the second inlet means of the present invention.

The patient delivery means 20 includes a mouthpiece means 21 having a mouth engagable portion at its axially outer end, around which the patient can place his lips to inspire medication from the chamber 56, and through which the patient can expire gasses. An inspiratory valve means 32 is coupled between the mouthpiece 21 and the chamber 56. The inspiratory valve 32 is configured for opening upon inspiration by the patient and closing upon expiration by the patient. An expiratory valve means 23 is coupled between the mouthpiece 21 and an exhaust means such as exhaust apertures 24, so that expiratory gasses will be exhausted to atmosphere, and externally of the chamber 56. As shown in FIG. 5B, the expiratory valve 23 is configured for opening upon expiration by the patient and, as shown in FIG. 5A for closing upon inspiration by the patient. A medication inlet means 40 is in fluid communication with the chamber 56. Medication can be introduced from the medication inlet means 40 into the chamber 56. The medication inlet means 40 includes a retaining means 44 (e.g. FIG. 1) or 46 (e.g. FIG. 11) for retaining the medication delivery means such as the delivery tube 47 (FIG. 9) of a medication inhaler onto the spacer 10.

As best shown in FIGS. 1–3, 5A and 5B the spacer body 30 includes a generally cylindrical wall 50 having a first end 52 and a second end 54. The cylindrical wall 50 has an interior surface 55 that defines the chamber 56. The first end 52 of the cylindrical wall 50 has a reduced diameter, axially extending annular flange 58 having an axial length of about 1 cm. A radially extending, generally planar valve seat member 60 is disposed adjacent to the first end 52 of the spacer body 30, and is recessed approximately 1 cm from the first end 52 of the spacer body 30.

The valve seat member 60 includes an axially inwardly facing first surface 61, and an axially outwardly facing second surface 63. A central aperture 62 is disposed in the middle of the radially extending valve seat member 60, and extends between the first and second surfaces 61, 63 respectively. A first ring of inspiratory flow apertures 64 are disposed radially outwardly of the central aperture 62, and comprise a generally annular array of apertures. A second ring of inspiratory flow apertures 66 are disposed radially outwardly of the first ring of aperture 64, and comprise a generally annular array of apertures.

The spacer body 50 can be variously sized to accommodate the particular needs for which it is intended. However, the applicant has found that a spacer body 30 having dimensions of approximately 50 mm in diameter and 185 mm in length advantageously provides an internal volume that is preferably about 250 ml, which is believed suitable for all age groups and sizes.

The patient delivery means 20 includes the inspiratory valve means. The inspiratory valve means includes the inspiratory valve member 32 and the radially extending valve seat member 60. The inspiratory valve 32 includes a radially extending disk shape portion 78 and an axially extending, plug-type retainer 80. In the embodiment shown in FIGS. 1 and 5A and 5B, the radially extending disk-shaped portion 78 and axially extending plug-type retainer 80 are molded from a one piece member which is preferably constructed from a heat sterilizable, light weight material such as "Silicone". The plug-type retainer 80 preferably includes a radially enlarged portion 81 disposed axially inwardly of the central aperture 62 for maintaining the plug-type retainer 80, and hence the valve 32 on the valve seat member 60. An example of such a valve member 32 is shown in Komesaroff U.S. patent application Ser. No. 08/490,779, which was filed on 14 May 1996 and which was invented by the same inventor and assigned to the same assignee as the present invention.

The radially extending disk-shaped portion 78 is designed to be light weight, and bendable under the pressure exerted by the patient's inspiration. The disk-shaped portion 78 is connected to the plug-type retainer 80 at its radially inner end, and has a generally free radially outward end 79. This construction enables the disk-shaped portion 78 to bend under the pressure exerted by inspiration, as shown in FIG. 5A. As the spacer 10 is designed for use by asthmatic patients who are having difficulty breathing, the inspiratory pressure that the patient is required to exert to bend the disk-shaped portion 78 is designed to be minimal. As the radially outer portion of the disk-shaped portion 78 is bendable, pressure can be exerted against it over a rather large area by inspiratory gasses flowing through the first and second rings inspiratory flow apertures 64, 66. This enables pressure to be exerted over a large portion of the surface of the disc-shaped portion 78, thus facilitating the bending of the disc-shaped portion 78 at very low pressures.

During times of neutral pressure and during times when the patient is expiring gasses, the disc-shaped portion 78 is placed in engagement with the valve seat member 60, as shown in FIG. 5B, to prevent the flow of gasses back into the chamber 56 through the inspiratory apertures 64, 66. As shown in FIG. 5A, the exertion of pressure in the chamber 56, or the exertion of inspiratory pressure by the patient causes the disc-shaped portion 78 to move away from valve seat member 60, to allow gasses to flow from the chamber 56, through the first and second ring of apertures 64, 66 and past the disc-shaped portion 78, in a direction indicated generally by (arrows 1).

Figure 2:
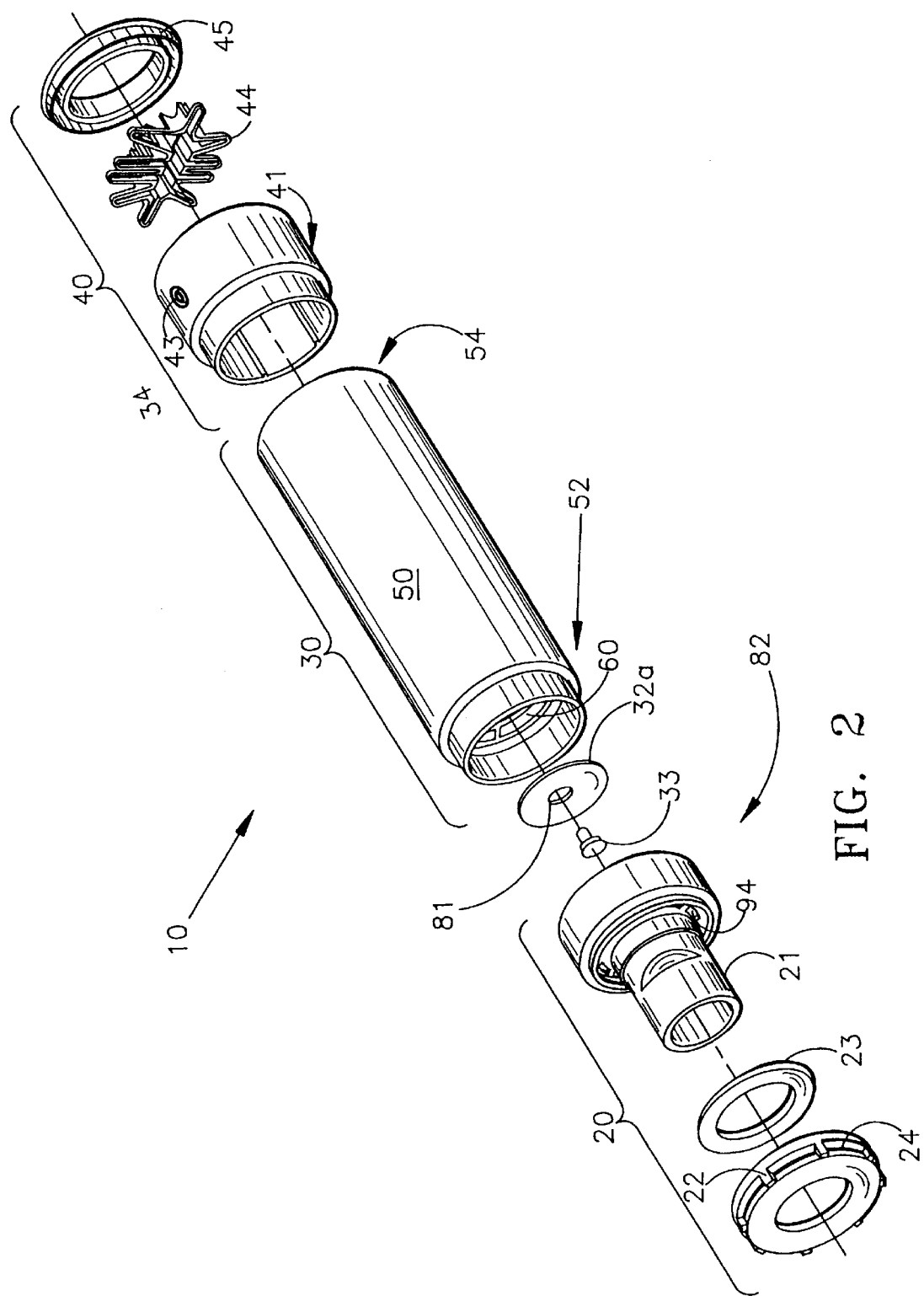
FIG. 2 illustrates an alternative embodiment of the spacer of the present invention.

An alternate embodiment valve member 32a is shown in FIG. 2. Valve member 32a comprises a washer-shaped disc having a central aperture 81. A separable retaining plug 33 is insertable through the central aperture 81, and is insertable through the central aperture 62 of the valve seat member 60 for retaining the disc-shaped valve member 32a on the valve seat member 60. Preferably, valve seat member 32a is constructed from a heat sterilizable material such as "Mylar" or "Teflon" material. It is believed that the advantage that can be obtained through the embodiment shown in FIG. 2 is that the washer-shaped disc 32a and retaining plug 33 may be less expensive to manufacture than the one-piece inspiratory valve 32 shown in FIG. 1, while still achieving similar performance characteristics.

Turning now to FIGS. 1–3, 5A, 5B and 10, the expiratory valve means is formed as a part of the patient delivery means 20, separate from the spacer body 30, and includes an expiratory valve housing 82 for containing the expiratory valve components. The expiratory valve components include a radially extending expiratory valve seat 84 which is formed as a part of the expiratory valve housing 82. The radially extending expiratory valve seat 84 includes an axially inwardly facing first surface 86 and an axially outwardly facing second surface. A centrally located, axially outwardly extending tube member 104 having an axially inner portion 96 is formed as a part of the valve seat 84 and defines a central aperture 92 in the valve seat 84. An annular ring of expiratory flow apertures 94 are disposed radially outwardly of, and surround the central aperture 92. An axially inwardly extending annular flange 98 is disposed radially outwardly of the expiratory flow apertures 94 and is sized for mating with the radially outwardly facing surface of the reduced diameter axially extending annular flange 58 of the spacer body 30. An annular positioning flange 99 extends axially outwardly from the second surface of valve seat 84, and is disposed radially outwardly of expiratory valve 23, for positioning the expiratory valve 23.

The expiratory valve member 23 is preferably an annular, washer-shaped leaflet that is constructed from an autoclavable and light weight material such as "Teflon". The expiratory valve 23 is movable between a closed position, as shown in FIG. 5A, wherein the expiratory valve 23 engages the valve seat 84, and an open position, (shown in FIG. 5B), wherein the unconnected expiratory valve 23 moves axially outwardly, to be placed in a spaced relation from the expiratory flow apertures 94 of the valve seat 84, to allow the flow of gasses therethrough, as designated by (arrows E). As will be noted in FIG. 5A, the engagement of the expiratory valve 23 with the axially outwardly facing second surface of the valve seat 84 causes the expiratory apertures 94 to be blocked, thus preventing the flow of gasses therethrough.

Figure 10:
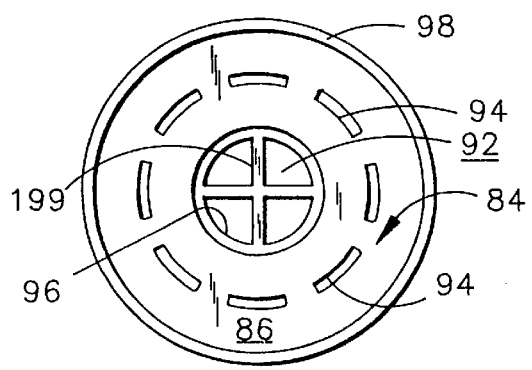
FIG. 10 is an end view of the valve seat of the expiratory valve of the present invention.

A closure cap member 22 is disposed axially outwardly of the expiratory valve housing 82. The closure cap 22 includes a central aperture through which tube 104 passes. Tube member 104 extends outwardly a sufficient distance to serve as the mouthpiece 21 of the spacer 10. Tube 104 includes an exterior surface 108, and an interior surface 110 which defines an interior passageway 112 through which inspiratory gasses (arrows 1) and expiratory gasses (arrows E) can pass. As shown in FIG. 10, the interior 112 of tube 104 of mouthpiece 21 preferably includes a cross bar member 199. Cross bar 199 is designed to prevent the inspiratory valve 32 from passing through the mouthpiece 21 if the valve member 32 retaining plug 81 becomes dislodged from aperture 62.

The axially outer end of the tube 104 comprises the mouth engagable mouthpiece 21 of the spacer 10. Preferably, the exterior surface should be generally oval in cross section to facilitate engagement of the mouthpiece 21 by the lips and mouth of the patient.

Figure 3:
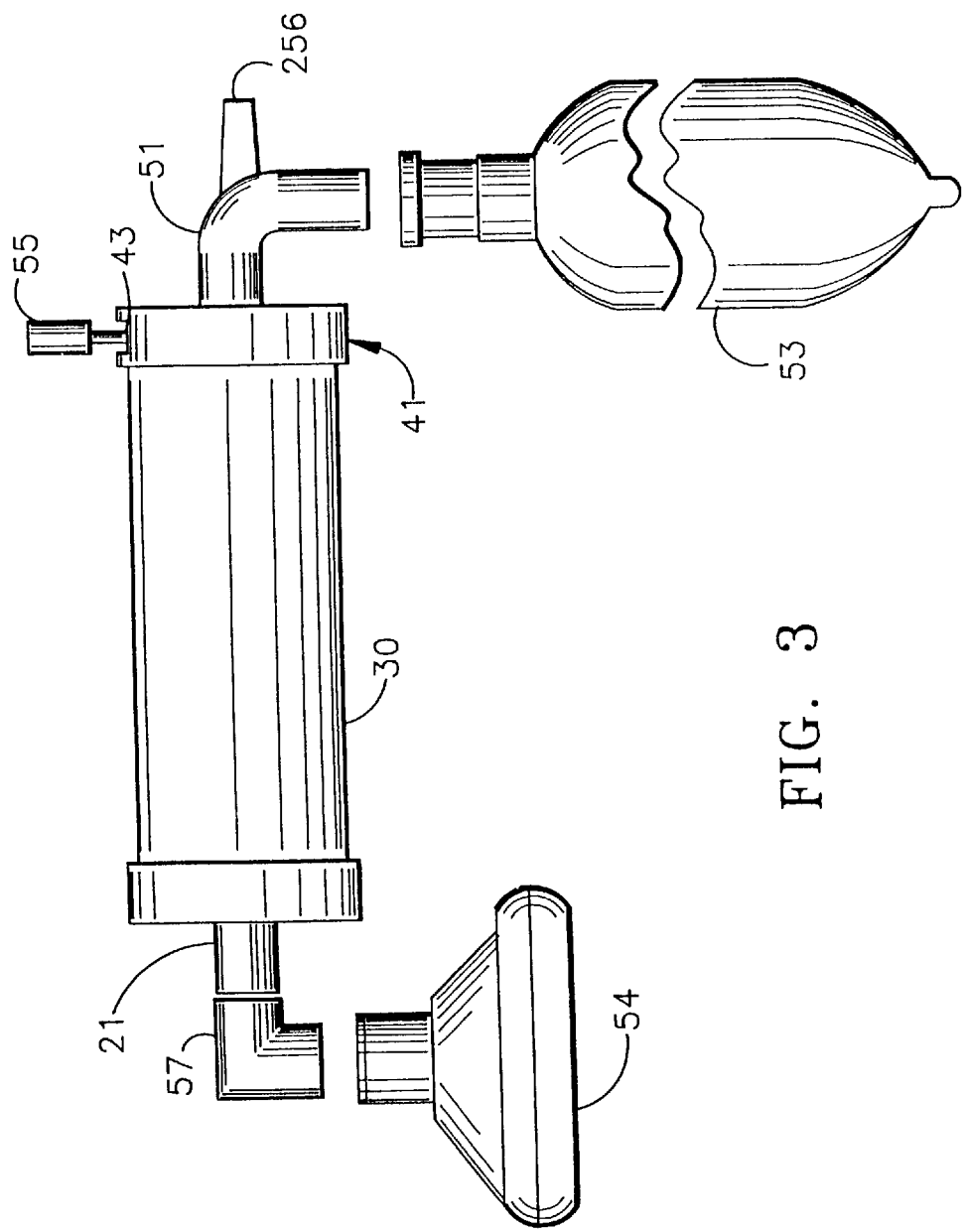
FIG. 3 illustrates a side schematic view of the spacer of the present invention when used in conjunction with an oxygen reservoir bag system.

In addition to being engagable by the mouth of the patient, the mouthpiece 21 can be coupled to a gas administration adaptor means, such as a face mask 54 (FIG. 3). As shown in FIG. 3, an elbow adaptor 57 can be used for coupling the mouthpiece 21 to the face mask 54. Other gas administration adaptor means can include such things as endotracheal tubes, laryngeal masks, and breathing circuits. To facilitate this connection, the exterior surface 108 of the tube member 104 is preferably sized for receiving 22 mm female gas administration device fittings, and the interior surface 110 is sized for receiving 15 mm male tapered gas administration fittings. Through this configuration, the mouthpiece 21 of the device allows for administration of medication at least five (5) different ways:

(1) Directly into the mouth through the lips of the patient engaging the outer surface 108 of the tube 104;

(2) Via a face mask having a 22 mm female taper fitting of the type typically found on adult face masks, which receives the outer surface 108 of the tube 104;

(3) Via a face mask having a 15 mm male taper fitting of the type typically found on child sized masks, wherein the 15 mm taper is received by the interior surface 110 of the tube 104;

(4) Via a 15 mm male taper fitting connector for an endotracheal tube or a laryngeal mask; and (5) Via appropriate international standard taper connectors for connection into a breathing circuit.

Closure cap 22 includes a radially extending portion 116 disposed radially outwardly of the tube member 104. The radially extending portion 116 terminates in an axially extending circumferential flange 118. The axially extending flange 118 includes an annular base 103 having a radially inwardly facing surface that frictionally engages the radially outwardly facing surface of positioning flange 99. Flange 118 also includes a circumferential array of exhaust apertures 24 formed therein. The axially inward end of the axially extending flange 118 is bonded to the axially outwardly facing periphery of the second surface of the valve seat member 84. Although the bonding can be done by a variety of means, sonic welding is the preferred method of attaching the closure cap 22 to the expiratory valve housing 82.

Closure cap 22 also includes an annular inner flange 117 that extends axially inwardly adjacent to the central aperture of the closure cap. The radially inwardly facing surface of the inner flange 117 frictionally engages the radially outwardly facing surface 110 of tube 104 to help secure the closure cap 22 to the expiratory valve housing 82. The axially inwardly facing end of the inner flange 117 is spaced from the axially outwardly facing surface of the expiratory valve 23, by 2–3 mm, to retain the valve 23 between the inner flange 117 and the axially outwardly facing second surface of the expiratory valve seat member 84. Although retained, the valve 23 is not clamped by the inner flange 117, thus allowing the unconnected valve 23 to move axially outwardly upon expiration, (FIG. 5B) and axially inwardly upon inspiration (FIG. 5A).

The inspiratory and expiratory valves operate in the following manner. The patient places his mouth over the exterior 108 of tube 104 of the mouthpiece 21, and inhales. The negative pressure exerted by the patient's inhalation causes the inspiratory valve 78 to bend axially outwardly, as shown in FIG. 5A, thus opening the portion of the first and second rings of inspiratory flow apertures 64, 66. This permits gasses within the chamber 56 to flow in a direction indicated generally by arrows I through the first and second rings of the inspiratory flow apertures 64, 66, into an inspiratory cavity 126, which is the space defined by the second surface 63 of the inspiratory valve seat 60, the radially inwardly facing surface of flange portion 58 of spacer body 50, the axially inwardly facing surface 86 of the expiratory valve seat 84, and the radially inwardly facing surface of tube member 96. The inspiratory gas flows through the inspiratory cavity 126, into the interior 112 of tube 104, and eventually into the mouth of the patient. At the same time, the negative pressure exerted by the patient's inspiration of gas pulls the expiratory valve 23 into engagement with the expiratory apertures 94 of the expiratory valve seat 84, thus cutting any fluid communication between the exhaust apertures 24 and the inspiratory cavity 126. As such, during inspiration, the gas being delivered to the patient is that gas from the chamber 56 and the inspiratory cavity 126. Virtually no gas is being delivered to the patient through the flow of gas through the exhaust apertures 24, as passage therethrough is blocked by the expiratory valve 23.

Upon expiration, a positive pressure is exerted by the patient so the gas travels in the direction generally indicated by the arrows E of FIG. 5B. Because of the relatively large surface area of the inspiratory valve disc portion 78, the pressure exerted during expiration pushes the disc portion 78 of the inspiratory valve into engagement with the axially outwardly facing surface 63 of the inspiratory valve seat member 60, so that the disc portion 78 covers the first and second rings of inspiratory flow apertures 64, 66, preventing the flow of gas therethrough. At the same time, the positive pressure exerted by the expiratory gasses causes the gas to flow through the expiratory apertures 94, to thereby exert force on the expiratory valve 23, to cause the expiratory valve 23 to float axially outwardly, thus moving the expiratory valve 23 away from its engagement with the expiratory valve apertures 94. The expiratory gas then flows into the expiratory cavity 128 and out to the atmosphere.

Expiratory cavity 128 is defined by the axially outwardly facing surface 88 of the valve seat 84, the inner flange 117, the radially inwardly facing surface 132 of the axially extending flange 118 of the closure cap 122, and the radially inwardly facing surface 134 of the radially extending portion 116 of the closure cap. It will be noted that the axially outwardly facing surface 108 of the tube 104, the axially inwardly facing surface of the inner flange, and the axially outwardly facing surface of the valve seat 84 serve as a positioning means for the expiratory valve 23, to maintain its proper orientation on the expiratory valve seat 84.

Figure 4:
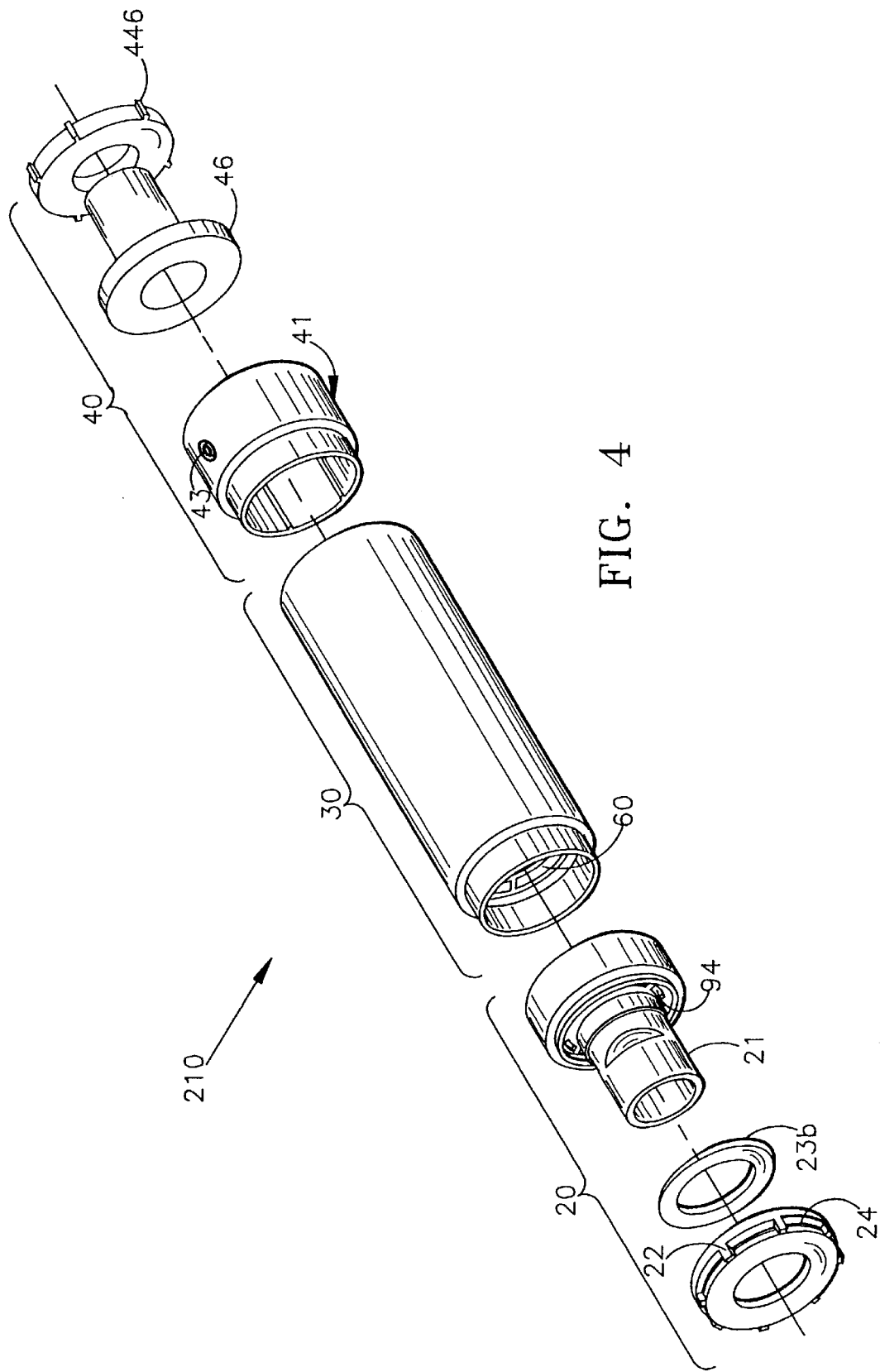
FIG. 4 illustrates a "pressure delivery" embodiment of the spacer of the present invention particularly well adapted for use in the hospital in a resuscitation, anaesthetic or intensive care breathing circuit.

As best shown in FIGS. 1 and 6–9, the medication inlet means 41 includes a generally cylindrical housing 144 having a reduced diameter annular flange 146 at its axially inner (first) end. The purpose of the flange 146 is for being received by the second end 54 of the spacer body 50, to mate the generally cylindrical medication inlet means housing 144 with the cylindrical wall 50 of the spacer body 30. The annular flange 146 is sized to be received snugly within the spacer body 50. The housing 144 includes a radially extending shelf member 152 having a central aperture 154. The housing 144 also includes an axially extending portion 156, which extends axially outwardly of the shelf member 152 so that the shelf member 152 becomes a recessed shelf member, which is not disposed at the second end of the medication inlet housing 144. The axially extending portion 156 includes a radially inwardly facing surface 157. The radially extending shelf member 152 also includes an axially outwardly facing surface 158 which serves as a seat for retaining means 44 or 46. In the embodiment shown in FIGS. 1, 2, 7 and 8, the retaining means comprises a retaining "battlement" spring 44. In FIGS. 4, 11 and 12, the retaining means comprises a "silicone grip" type retaining means 46.

A closure cap member 45 is disposed axially outwardly of the radially extending shelf member 152. The closure cap member 45 includes a radially extending portion 162, and a reduced diameter axially extending portion 164 which defines a central aperture in the closure cap member 45.

The retaining battlement spring 44 has a serpentine base portion 170. Base portion 170 includes a plurality of radially outwardly disposed portions 172 that alternate with a plurality of radially inwardly disposed portions 174. Axially extending fingers 178 are formed at each of the radially inwardly disposed portions 174. Each of the axially extending fingers 178 includes a radially inwardly facing gripping surface 180. Each of the radially inwardly facing gripping surfaces 180 include a beveled portion 182 adjacent to their axially outwardly facing ends. The beveled surfaces 182 of the plurality of finger members 178 are configured to form a funnel-like opening having a relatively larger diameter adjacent to the axially outer ends of the fingers 178, and a relatively smaller diameter adjacent to the axially inner ends of the fingers 178. The spring 44 can be coated with an autoclavable gripping material to enhance its gripping qualities. Alternately, the spring retaining means 44 can have a different shape or size to accommodate particular shapes and sizes of medication delivery tubes.

Figure 7:
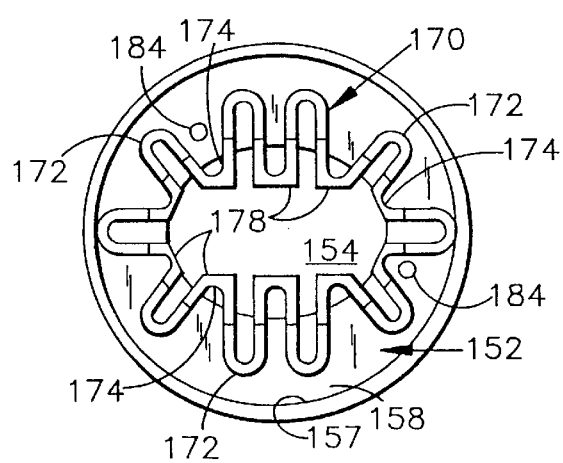
FIG. 7 is an end view of the medication inlet means of an embodiment containing the retaining spring of the present invention.

The serpentine 170 base causes the spring 44 to have spring-like qualities wherein a central opening of the spring 44 defined by the axially extending fingers 178 and the radially inwardly disposed portions 174 can expand if an object, such as a delivery tube 47 of a medication inhaler is inserted therein. Turning now to FIG. 7, it will be noticed, that a substantial gap exists between the radially outwardly disposed portions 172 of the serpentine base 170 and the radially inwardly facing surface 157 of the axially extending portion 156 of the cylindrical housing 144. However, it will also be noticed that the radially extending shelf member 152 extends radially inwardly far enough to serve as a seat for the serpentine base 170, and in particular for the radially outwardly disposed portion 172 of the serpentine base 170, when the spring 44 is in its relaxed position as shown in FIG. 7.

Figure 8:
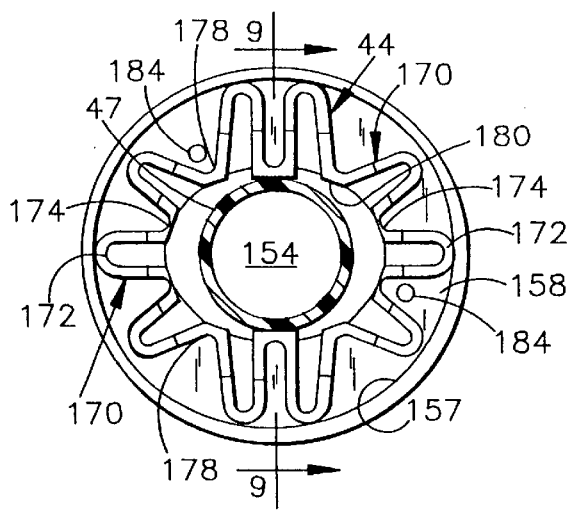
FIG. 8 is a end view of the medication inlet means of an embodiment containing the retaining spring of the present invention showing a medication delivery means inserted therein.
Figure 9:
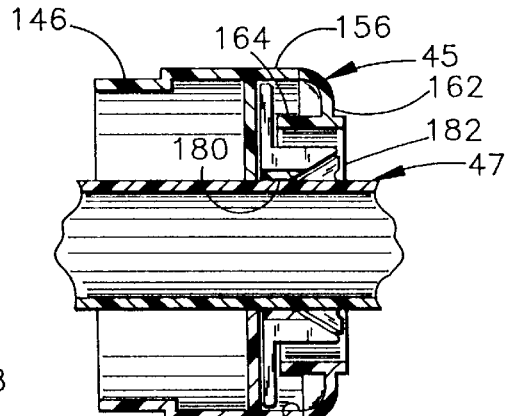
FIG. 9 is a sectional view taken along lines 9—9 of FIG. 8.

FIGS. 8 and 9 show the relative position of the spring 44 when a medication delivery tube 47 is inserted through the axially extending fingers 178, and into the central aperture 154 of the radially extending shelf 152. The insertion of the medication delivery tube 47 into the central aperture 154 causes the radially outwardly facing surface of the medication delivery tube 47 to engage the gripping surfaces 180 of the axially extending fingers 178. The insertion of the delivery tube 47 expands the effective diameter of the opening formed by the plurality of axially extending fingers 178, which causes the serpentine base 170 to move radially outwardly. As best shown in FIG. 8, the radially outward movement of the serpentine base 170 caused by the insertion of a medication delivery tube 47 causes the radially outwardly disposed portions 172 of the serpentine base 170 to move much closer to the radially inwardly facing surface 157.

The axially extending fingers 178 can move semi-independently of each other, so that the gripping surfaces can accept delivery tubes 47 of different shapes and sizes. In this regard, it has been found by the applicant that a serpentine ring having an oval-shaped opening formed by its axially extending fingers 178 which has a dimension, when in its relaxed position of approximately 3 cm along its long axis and 1.5 cm along its short axis, but which is expandable to have an expanded diameter of about 3.5 cm along its long axis and about 2 cm along its short axis, can accommodate most, if not all, of the various shapes and sizes of medication inhalers currently on the market.

By accommodating these inhaler delivery tubes 47, the retaining spring 49 (FIGS. 1,2,7 and 8) or silicone grip 46 (FIGS. 4, 11 and 12), are each small enough to grip the inhaling tube 47 securely, but large enough to accept it fully. Additionally, both the spring 44 and silicone grip 46 are sized to properly receive and grip an elbow of an oxygen line (e.g. elbow 51 of FIG. 3) so that oxygen can be the medication delivered to the chamber 56 through the primary medication inlet.

To help maintain the retaining spring 44 in its proper rotational position, one or more axially extending projections 184 may be formed in the axially outwardly facing surface 158 of the radially extending shelf 152. The projections 184 help to prevent the retaining spring 44 from rotating on the shelf 152. Similar projections serve a similar purpose for silicone retaining grip 46 of the embodiment shown in FIGS. 11 and 12.

As best shown in FIGS. 1–4 and 6, the cylindrical housing 144 may include a second medication inlet means 43 that is also in fluid communication with the chamber 56. Second inlet 43 allows a gas line, such as oxygen to be attached in fluid communication with the chamber 56 to enable the simultaneous administration of oxygen and aerosol medication through the second 43 and first 31 medication inlets. This is particularly important in patients with recurring severe asthma and when medication is required during resuscitation, anesthetic administration, and intensive care. Alternately, the nozzle or outlet of the cartridge of a metered dose inhaler can be inserted into the second medication inlet 43, and higher concentrations of oxygen can be introduced, using for example an elbow nipple means (e.g. elbow 51 of FIG. 3) which is connected to a breathing bag (e.g. breathing bag 53 of FIG. 3), wherein the elbow nipple means is inserted through the retaining spring 44, (or silicone retaining grip 46) and into the central aperture 154 of the medication inlet means 40. When the metered dose inhaler is attached to the second inlet 43, it is preferably accomplished by inserting the male nozzle of cartridge into the passageway of nipple 186, so that nipple 186 serves as a female receptor for the "male" cartridge nozzle.

The second medication inlet includes a radially extending nipple member 186 which is disposed in a counter-sunk bowl member 188. The nipple 186 is sized for being received by an oxygen line, and includes an interior passageway having a second end in fluid communication with the chamber 56. Bowl member 188 serves to aid in maintaining the oxygen line on the nipple 186, and also serves to protect the nipple 186 from breakage. It has been found by applicant that superior results are achieved if the second end opening 192 is designed to direct the medication in an axial direction toward the patient delivery means, rather than a radial direction.

The entire spacer unit 10, is preferably made of a high impact, heat sterilizable material and in particular, a heat sterilizable plastic material.

An alternate embodiment retaining means configuration is shown in FIGS. 11 and 12. Turning now to FIGS. 11 and 12, the medication inlet end of a spacer is shown, which includes a spacer body 450, a cylindrical housing 444, a retaining means which comprises a ring-shaped silicone grip 46, and a closure cap 445. The alternate embodiment spacer is provided for receiving the delivery tube 447 of a medication inhaler 448. Additionally, the spacer shown in FIGS. 11 and 12 may include a patient end similar to that shown in FIGS. 1, 5A and 5B.

As will be noticed, many of the components set forth above are similar to their counterpart components shown in FIGS. 1, 2, and 6–10. The spacer body 450 is generally similar to spacer body 50 of the embodiment shown in FIGS. 1, 2, and 7–9. Further, the closure cap 445 is generally similar to closure 45 shown in FIGS. 1, 2, and 9. Also, medication inhaler 448 and its delivery tube 447 are similar to the delivery tube 47 and medication inhaler (not shown) that are discussed above.

It will be appreciated that the cross sectional shape of the delivery tube 447 will vary, as a large number of different shaped medication inhalers exist. The primary shapes of the medical inhalers known to the applicant include an oval shaped tube, a round shaped tube, and a tube which consist of a pair of opposed concave surfaces joined together at a pair of opposed points. Importantly, the silicone grip 46 is sized, shaped, and is sufficiently elastic to snugly receive these known shapes of delivery tubes.

The cylindrical housing 444 of FIGS. 11 and 12, while generally similar to cylindrical housing 144, has some differences. The similarities include the fact that the size and shape of the exterior wall of the cylindrical housing 444 is generally similar to its counterpart 41, along with the fact that it includes a second medication inlet means 443 that is generally identical to the second medication inlet means 43 of FIGS. 1–4 and 6. The cylindrical housing 444 also includes a radially extending shelf member 452 having axially extending projections 484 that are similar to projections 184, and a central aperture 454 that is virtually identical to the central aperture 154. Additionally, cylindrical housing 444 includes two axially extending, spaced retaining fingers 455, 456 that extend through the aperture 454, and which are provided for gripping the delivery tube 447, when it is inserted into aperture 454 to help maintain the position of the tube 447 within the aperture 454. The spaced retaining fingers 455, 456 are placed within the central aperture 454 approximately 180° from each other, to be generally placed across from each other in an opposed relation.

The silicone grip 46 includes a washer-shaped base portion 470 having a pair of opposed "flats" 469 for side surfaces. The base portion 470 has divots 485 formed on its underside for receiving the axially extending projections 484 that are formed on the radially extending shelf 452, for maintaining the base 470, and hence the silicone grip 46 in its proper rotational orientation. The base 470 has a tube-like open central portion, which is defined by an axially extending cylindrical portion 471 of the silicone grip 46. The cylindrical portion 471 extends axially outwardly, and terminates in a radially extending shelf portion 473 having a truncated-oval shaped aperture therein for receiving the delivery tube 447. When the silicone grip 46 is positioned properly on the radially extending shelf 452, the axially extending retaining fingers 455 are disposed within the interior of the cylindrical portion 471, and are positioned adjacent to the opposed "flats" portions (not shown) of the truncated-oval shaped aperture 487. When so positioned, the fingers 455, 456 are well placed for receiving the delivery tube 447 of the medication inhaler 448. The pair of opposed "flats" portions of the truncated-oval shaped aperture of the shelf portion 473 extend generally parallel to the flats 469 of the side surface of the base portion 470. The silicone grip 46 is made from an elastomeric silicone material to be generally elastic and pliable to permit the central aperture 487 of the ring to be expandable to receive a delivery tube 447 and to elastically grip the delivery tube 447.

FIG. 3 illustrates the "domestic" spacer of either FIGS. 1 or 2 which can be used by a doctor in an emergency situation in a breathing patient and used when higher concentrations of oxygen are required or desired. A face mask 54, is connected directly to mouthpiece 21, or via a connection means 57, which is preferably an elbow, to patient inlet/outlet means 21, of the spacer body 30. The connection means 57, preferably has a 22 mm male, or 15 mm female connection to the face mask 54 and preferably a 15 mm male connection or a 22 mm female connector to the patient inlet/outlet means 21. At the medication inlet means 41, another connection means 51, which is also preferably an elbow inserts into the medication inlet means 41. The other end of the elbow 51 is fitted into a breathing bag 53. The connection means 51, preferably has 22 mm male fittings at each end. An inlet nipple port 256, on the connection means 51, enables the supply of a high concentration of oxygen to the patient. The nozzle of the medication cartridge 55, fits into port 43, of the base portion 41, of the medication inlet means 40. Thus in an emergency when the doctor is treating a patient, not necessarily in a hospital environment, the doctor is able to administer the medication and higher concentrations of oxygen simultaneously.

A modified spacer 210 intended primarily for professional use is shown in FIG. 4, which is used in a resuscitation, anaesthesia or an intensive care breathing circuit for positive pressure ventilation. In these circumstances, the inspiratory valve means 32 is omitted and the expiratory valve means 23 is replaced preferably by a closure disc 23b which fills the cavity between the expiratory valve retaining means 22 and the mouthpiece 21, to prevent release of the patient expired gases from the spacer 210 via apertures 24. FIG. 4 illustrates the embodiment where the disc 23b is used. With further reference to FIG. 4, when the spacer 210, is to be inserted into an anaesthetic, intensive care or resuscitation breathing circuit, the base portion 41, accommodates an alternate embodiment retaining means 46 (preferably made from silicone), in place of the retaining spring 44, and closure cap member 45. (The silicone grip 46 of FIG. 4 is virtually identical to the grip 46 of FIGS. 11 and 12 discussed above.) The spacer 210, may then be made part of an anaesthetic, intensive care or resuscitation breathing circuit, or oxygen can be introduced, using for example, an elbow nipple means (similar to elbow 51 of FIG. 3), which is connected to a breathing bag (similar to the breathing bag of FIG. 3), inserted into the fitting 46. Because of the lack of inspiratory and expiratory valves in the embodiment of FIG. 4, gasses flowing through the chamber can not escape into the atmosphere through the expiratory apertures. As such, the spacer 210 of FIG. 4 enables the health care provider to exert a positive gaseous pressure into the patient. This ability to exert positive pressure is especially useful in patients who are not breathing on their own, such as patients who are under an anesthetic. In such cases, the provision of the second inlet 43 allows medication to be introduced simultaneously into the chamber 56, and hence into the patient.

During use with a non-breathing patient, the spacer of FIG. 4 would normally be attached to either a face mask, breathing circuit, laryngeal mask or endotracheal tube at its patient delivery end, and an oxygen (or anesthetic) delivery tube (or breathing bag) at its medication inlet end. In such a case, the spacer of FIG. 4 could have an outward appearance similar to the spacer of FIG. 3.

Thus the present invention provides an improved multi functional spacer for the administration of medications, such as pharmaceutical products, air, and oxygen, which can be used both domestically and professionally and also which allows the simultaneous supply of additional gases (preferably oxygen) to the patient along with the aerosol medication. Also the improved spacer of the invention, which is to be promoted as the SPACE CHAMBER™ spacer, enables easier inhalation and exhalation, than any of the existing spacer arrangements, due to its reduced flow resistance, when compared to other known spacers. Further, a modified version enables the space chamber to be used as a part of, or in conjunction with a breathing circuit.

What is claimed is:

1. A spacer for the administration of an aerosol medication to a patient comprising:
   (1) a spacer body member defining a generally hollow chamber,
   (2) a patient delivery member in fluid communication with the chamber through which medication can be delivered to a patient, the patient delivery member including
      (a) a mouthpiece through which a patient can inspire medication from the chamber and expire gases,
      (b) an inspiratory valve coupled between the mouthpiece and the chamber, the inspiratory valve being configured for opening on inspiration by a patient, and closing upon expiration by a patient,
      (c) an expiratory valve coupled between the mouthpiece and an exhaust external of the chamber, and disposed co-axially with the inspiratory valve, the expiratory valve configured for opening upon expiration by a patient, and closing upon inspiration by a patient, and
   (3) a medication inlet in fluid communication with the chamber through which medication can be introduced to the chamber, the medication inlet including a dispenser retainer for retaining a medication delivery member on the medication inlet.

2. The spacer of claim 1 wherein the inspiratory valve includes a generally planar inspiratory valve seat having a plurality of valve seat apertures, and a disc shaped inspiratory valve member for selectively covering said apertures, the inspiratory valve member including a valve retainer for fixedly coupling the inspiratory valve member to the inspiratory valve seat, further comprising a cross-bar disposed in the mouthpiece for preventing inspiration of the inspiratory valve member.

3. The spacer of claim 1 wherein the inspiratory valve includes an inspiratory valve member having a valve retainer, and a generally planar inspiratory valve seat having a central aperture for receiving the valve retainer, and a plurality of flow apertures disposed radially outwardly of the central aperture through which gas can pass.

4. The spacer of claim 3 wherein the inspiratory valve member includes
  (1) a centrally disposed valve retainer insertable through the central aperture for fixedly coupling the inspiratory valve member to the inspiratory valve seat,
  (2) a peripheral edge disposed radially outwardly from the valve retainer, and
  (3) a valve flap portion disposed between the valve retainer and the peripheral edge for selectively covering the flow apertures, the valve flap portion being sufficiently bendable under the pressure exerted by a patient's inspiration to uncover the flow apertures to allow the flow of gases therethrough.

5. The spacer of claim 4 wherein:
  (1) the inspiratory valve member includes a central aperture alignable with the central aperture of the valve seat;
  (2) the valve retainer is formed separately from the inspiratory valve member; and
  (3) the valve retainer can be inserted through the central aperture of the inspiratory valve member for coupling the inspiratory valve member to the inspiratory valve seat.

6. The spacer of claim 4 wherein the expiratory valve includes a generally planar expiratory valve seat having an annular array of flow apertures, and an annular expiratory valve member movable between an opened position out of engagement with the flow apertures upon expiration by a patient and a closed position in engagement with the flow apertures upon inspiration by a patient.

7. The spacer of claim 6 wherein the expiratory valve seat includes a central aperture disposed radially inwardly of the flow apertures, further comprising an annular, axially extending positioning member disposed radially inwardly of the flow apertures.

8. The spacer of claim 7 wherein the mouthpiece means includes a tube extending axially outwardly from the central aperture of the valve seat, wherein the tube includes a mouth engageable portion.

9. A spacer for the administration of an aerosol medication to a patient comprising:
  (1) a spacer body member defining a generally hollow chamber,
  (2) a patient delivery member in fluid communication with the chamber through which medication can be delivered to a patient, the patient delivery member including
    (a) a mouthpiece through which a patient can inspire medication from the chamber and expire gases,
    (b) an inspiratory valve coupled between the mouthpiece and the chamber, the inspiratory valve being configured for opening on inspiration by a patient, and closing upon expiration by a patient,
    (c) an expiratory valve coupled between the mouthpiece and an exhaust external of the chamber, the expiratory valve configured for opening upon expiration by a patient, and closing upon inspiration by a patient, the expiratory valve including
      (i) a generally planar expiratory valve seat having an annular array of flow apertures, and a central aperture disposed radially inwardly of the flow apertures,
      (ii) an annular expiratory valve member movable between an opened position out of engagement with the flow apertures upon expiration by a patient and a closed position in engagement with the flow apertures upon inspiration by a patient, and
      (iii) an axially extending positioning member disposed radially inwardly of the flow apertures;
    wherein the mouthpiece includes a tube extending axially outwardly from the central aperture of the expiratory valve seat.
  (3) a medication inlet in fluid communication with the chamber through which medication can be introduced to the chamber, the medication inlet including a dispenser retainer for retaining a medication delivery member on the medication inlet; and
  (4) a closure cap member disposed axially outwardly of the expiratory valve seat, the closure cap member including a central aperture through which the tube can pass, exhaust apertures through which expiratory gas can pass, and an axially extending portion for engaging the valve seat.

10. A spacer for the administration of an aerosol medication to a patient comprising:
  (1) a spacer body member defining a generally hollow chamber,
  (2) a patient delivery member in fluid communication with the chamber through which medication can be delivered to a patient, the patient delivery member including
    (a) a mouthpiece through which a patient can inspire medication from the chamber and expire gases,
    (b) an inspiratory valve coupled between the mouthpiece and the chamber, the inspiratory valve being configured for opening on inspiration by a patient, and closing upon expiration by a patient,
    (c) an expiratory valve coupled between the mouthpiece and an exhaust external of the chamber, the expiratory valve configured for opening upon expiration by a patient, and closing upon inspiration by a patient, the expiratory valve including:
      (i) a valve seat having flow apertures therethrough, the valve seat comprising a generally radially extending member having a first surface, a second surface, and central aperture, the flow apertures comprising an annular array of flow apertures disposed radially outwardly of the central aperture and extending between the first and second surfaces of the valve seat member;
      (ii) a valve member movable between an opened position out of engagement with the flow apertures upon expiration by a patient, and a closed position in engagement with the flow apertures upon inspiration by a patient; the valve member comprising an annular valve member disposed adjacent to the second surface of the valve seat; and (iii) a positioner for maintaining the valve member adjacent to the flow apertures of the valve seat member; and (3) a medication inlet in fluid communication with the chamber through which medication can be introduced to the chamber, the medication inlet including a dispenser retainer for retaining a medication delivery member on the medication inlet.

11. The spacer of claim 10 wherein the positioner includes a closure cap member having an axially inwardly extending flange for engaging a surface of the expiratory valve member, for retaining the expiratory valve member between the axially inwardly extending flange and the expiratory valve seat.

12. The spacer of claim 11 wherein the closure cap member includes an axially extending portion having an axially inwardly facing surface disposed in opposition to the expiratory valve seat, and the exhaust apertures are formed on the closure cap member for allowing expiratory gas to be exhausted from the exhaust cavity.

13. The spacer of claim 10 wherein the expiratory valve seat includes an axially outwardly extending tube member for forming said mouthpiece, for conducting gasses between a patient and a space adjacent the first surface of the expiratory valve seat.

14. The spacer of claim 1 wherein the mouthpiece includes an end portion sized for being mateable with a gas administration adaptor.

15. The spacer of claim 14 wherein the mouthpiece end portion includes an exterior surface sized for being mateable with at least one of a face mask and breathing circuit.

16. The spacer of claim 14 wherein the mouthpiece end portion includes an interior surface sized for receiving at least one of an endotracheal tube, laryngeal mask, and child sized face mask.

17. The spacer of claim 14 wherein the mouthpiece end portion includes an inner diameter sized for receiving a 15 mm male connector for a gas administration adaptor, and an outer diameter sized for receiving a 22 mm female connector for a gas administration adaptor.

18. The spacer of claim 1 wherein the dispenser retainer includes a base portion having a diameter expandable between a relaxed position and an expanded position, for gripping the medication delivery.

19. A spacer for the administration of an aerosol medication to a patient comprising:

(1) a spacer body member defining a generally hollow chamber, (2) a patient delivery member in fluid communication with the chamber through which medication can be delivered to a patient, the patient delivery member including (a) a mouthpiece through which a patient can inspire medication from the chamber and expire gases, (b) an inspiratory valve coupled between the mouthpiece and the chamber, the inspiratory valve being configured for opening on inspiration by a patient, and closing upon expiration by a patient, (c) an expiratory valve coupled between the mouthpiece and an exhaust external of the chamber, the expiratory valve configured for opening upon expiration by a patient, and closing upon inspiration by a patient, and '(3) a medication inlet in fluid communication with the chamber through which medication can be introduced to the chamber, the medication inlet including a dispenser retainer for retaining a medication delivery member on the medication inlet, the dispenser retainer including a base portion comprising a serpentine ring member having a plurality of radially outwardly disposed portions, and a plurality of radially inwardly disposed portions, and a plurality of axially extending finger members for gripping the medication delivery means, wherein the finger members extend axially outwardly from the radially inwardly disposed portions.

20. The spacer of claim 19 wherein the finger members include an axially inner end, an axially outer end, and a beveled gripping surface extending at least partially between the axially inner end and axially outer end, the beveled surfaces of the plurality of finger members, being configured to form a funnel-like opening having a relatively larger diameter adjacent to the axially outer ends of the fingers, and a relatively smaller diameter adjacent to the axially inner ends of the fingers.

21. A spacer for the administration of an aerosol medication to a patient comprising:

(1) a spacer body member defining a generally hollow chamber, (2) a patient delivery member in fluid communication with the chamber through which medication can be delivered to a patient, the patient delivery member including (a) a mouthpiece through which a patient can inspire medication from the chamber and expire gases, (b) an inspiratory valve coupled between the mouthpiece and the chamber, the inspiratory valve being configured for opening on inspiration by a patient, and closing upon expiration by a patient, (c) an expiratory valve coupled between the mouthpiece and an exhaust external of the chamber, the expiratory valve configured for opening upon expiration by a patient, and closing upon inspiration by a patient, and (3) a medication inlet in fluid communication with the chamber through which medication can be introduced to the chamber, the medication inlet including a dispenser retainer for retaining a medication delivery member on the medication inlet the dispenser retainer including a base portion having a diameter expandable between a relaxed position and an expanded position, for gripping the medication delivery, the medication inlet including a housing having an axially extending portion and a shelf portion sized for receiving the base portion of the dispenser retainer, and being sized to support the base portion in each of its relaxed and expanded positions.

22. The spacer of claim 21 wherein the shelf portion comprises a radially extending member having a central aperture through which medication can be introduced into the chamber.

23. The spacer of claim 21 wherein the medication inlet includes a radially extending cap member disposed axially outwardly of the shelf portion, axially extending portion and shelf portion being configured for capturing the base portion for maintaining it on the medication inlet.

24. The spacer of claim 22 wherein the closure member includes a central aperture for receiving the axially extending fingers of the dispenser retainer, the central aperture having an inner diameter small enough to restrain axial movement of the base portion when in its relaxed position, and large enough to accommodate the base portion when in its expanded position.

25. A spacer for the administration of an aerosol medication to a patient comprising:

(1) a spacer body member defining a generally hollow chamber,
(2) a patient delivery member in fluid communication with the chamber through which medication can be delivered to a patient, the patient delivery member including
  (a) a mouthpiece member through which a patient can inspire medication from the chamber and expire gases,
  (b) an inspiratory valve coupled between the mouthpiece and the chamber, the inspiratory valve being configured for opening on inspiration by a patient, and closing upon expiration by a patient,
  (c) an expiratory valve coupled between the mouthpiece and an exhaust external of the chamber, the expiratory valve configured for opening upon expiration by a patient, and closing upon inspiration by a patient, and
(3) a medication inlet in fluid communication with the chamber through which medication can be introduced to the chamber, the medication inlet including a dispenser retainer for retaining a medication delivery member on the medication inlet, the medication inlet including a housing having a generally tubular axially extending portion mateable with the spacer body member and in fluid communication with the chamber, and a radially extending cap member having a central aperture sized for receiving a tubular medication delivery member, the housing and cap member being configured for capturing the dispenser retainer therebetween.

26. The spacer of claim 1 further comprising a second medication inlet in fluid communication with the chamber for providing a second medication to the patient.

27. The spacer of claim 26 wherein the second medication inlet includes a nipple for receiving a cartridge of a medication delivery tube.

28. A spacer for the administration of an aerosol medication to a patient comprising:
(1) a spacer body member defining a generally hollow chamber,
(2) a patient delivery member in fluid communication with the chamber through which medication can be delivered to a patient, the patient delivery including
  (a) a mouthpiece through which a patient can inspire medication from the chamber and expire gases,
  (b) an inspiratory valve coupled between the mouthpiece and the chamber, the inspiratory valve being configured for opening on inspiration by a patient, and closing upon expiration by a patient,
  (c) an expiratory valve coupled between the mouthpiece and an exhaust external of the chamber, the expiratory valve configured for opening upon expiration by a patient, and closing upon inspiration by a patient,
(3) a first medication inlet in fluid communication with the chamber through which medication can be introduced to the chamber, the medication inlet including a dispenser retainer for retaining a medication delivery member on the medication inlet; and
(4) a second medication inlet in fluid communication with the chamber for providing a second medication to the patient the second medication inlet including a recessed bowl portion disposed on a side portion of the spacer, adjacent to the medication inlet, and a radially extending nipple for receiving an oxygen line disposed within the bowl portion.

29. The spacer of claim 26 wherein the medication inlet is configured for receiving an oxygen supply, and the second medication inlet is configured for receiving an outlet of a medication cartridge.

30. The spacer of claim 28, wherein the second medication inlet includes a radially directed passageway for receiving the second medication, and an axially extending passageway for delivering the second medication to the chamber.

31. A spacer for the administration of an aerosol medication to a patient comprising:
(1) a spacer body member defining a generally hollow chamber,
(2) a patient delivery member in fluid communication with the chamber through which medication can be delivered to a patient, the patient delivery member including
  (a) a mouthpiece through which a patient can inspire medication from the chamber and expire gases,
  (b) an inspiratory valve coupled between the mouthpiece and the chamber, the inspiratory valve being configured for opening on inspiration by a patient, and closing upon expiration by a patient,
  (c) an expiratory valve coupled between the mouthpiece and an exhaust external of the chamber, the expiratory valve configured for opening upon expiration by a patient, and closing upon inspiration by a patient, and
(3) a medication inlet in fluid communication with the chamber through which medication can be introduced to the chamber, the medication inlet including a dispenser retainer for retaining a medication delivery member on the medication inlet, the medication inlet including a housing for housing the dispenser retainer, the housing being coupled to the spacer body, the dispenser retainer including a base portion for coupling the dispenser retainer to the housing and a central aperture for receiving the medication delivery member.

32. The spacer of claim 31 wherein the dispenser retainer is comprised of a grip member formed from an elastomeric material for permitting the central aperture to expand to receive and grip the medication delivery member.

33. A spacer for the administration of an aerosol medication to a patient comprising:
(1) a spacer body member defining a generally hollow chamber,
(2) a patient delivery member in fluid communication with the chamber through which medication can be delivered to a patient, the patient delivery member including
  (a) a mouthpiece through which a patient can inspire medication from the chamber and expire gases,
  (b) an inspiratory valve coupled between the mouthpiece and the chamber, the inspiratory valve being configured for opening on inspiration by a patient, and closing upon expiration by a patient,
  (c) an expiratory valve coupled between the mouthpiece and an exhaust external of the chamber, the expiratory valve configured for opening upon expiration by a patient, and closing upon inspiration by a patient, and
(3) a medication inlet in fluid communication with the chamber through which medication can be introduced to the chamber, the medication inlet including a dispenser retainer formed of an elastomeric material for retaining a medication delivery member on the medication inlet, the medication inlet including a housing for housing the dispenser retainer, the dispenser retainer including a base portion for coupling the dispenser retainer to the housing and a central aperture for receiving the medication delivery member, the housing further comprising at least one resilient retaining finger disposed adjacent the central aperture of the dispenser retainer for gripping the medication delivery member, the retaining finger being formed from a non-elastomeric material.

34. The spacer of claim 33 wherein the retaining finger comprises a pair of opposed retaining finger members connected to the housing, and the housing is coupled to the spacer body.

35. A spacer for the administration of an aerosol medication to a patient comprising:
   (1) a spacer body member defining a generally hollow chamber,
   (2) a patient delivery member in fluid communication with the chamber through which medication can be delivered to a patient, the patient delivery member including
      (a) a mouthpiece through which a patient can inspire medication from the chamber and expire gases, '(b) an inspiratory valve coupled between the mouthpiece and the chamber, the inspiratory valve being configured for opening on inspiration by a patient, and closing upon expiration by a patient,
      (c) an expiratory valve coupled between the mouthpiece and an exhaust external of the chamber, the expiratory valve configured for opening upon expiration by a patient, and closing upon inspiration by a patient, and
   (3) a medication inlet in fluid communication with the chamber through which medication can be introduced to the chamber, the medication inlet including a dispenser retainer for retaining a medication delivery member on the medication inlet, the dispenser retainer including a base portion and a central aperture for receiving the medication delivery, the medication inlet including a housing for housing the dispenser retainer, further comprising a projection formed on one of the housing and dispenser retainer; and a divot formed on the other of the housing and dispenser retainer, the divot and dispenser retainer being cooperable for preventing movement of the dispenser retainer and housing relative to each other.

36. The spacer of claim 31 wherein the dispenser retainer includes an axially extending tube like portion coupled to the base portion, and a radially extending shelf portion, the central aperture being formed in the radially extending shelf portion.

37. A spacer for the administration of an aerosol medication to a user comprising:
   (1) a spacer body member defining a generally hollow chamber, the spacer body having a first end and a second end;
   (2) a patient delivery member disposed adjacent to the first end of the spacer body, the patient delivery member being in fluid communication with the chamber through which medication can be delivered to a patient, the patient delivery member including a mouthpiece through which a patient can inspire medication from the chamber and expire gases, the mouthpiece being configured for mating with a gas administrator,
   (3) a first medication inlet disposed adjacent to the second end of the spacer body the first medication inlet being in fluid communication with the chamber through which medication can be introduced to the chamber, the first medication inlet including a dispenser retainer for retaining a medication delivery member on the first medication inlet, the first medication inlet including a separable housing, the housing being selectively coupled to the second end of the spacer body and
   (4) a second medication inlet coupled to the housing adjacent to the second end of the spacer body, the second medication inlet means being in fluid communication with the chamber through which a second medication can be introduced into the chamber, the second medication inlet including a nipple adapted for receiving a gas line.

38. The spacer of claim 10, further comprising a second medication inlet that includes a nipple adapted for receiving a cartridge of a medication delivery tube.

39. The spacer of claim 10, further comprising a second medication inlet that includes a nipple adapted for receiving a gas line.

* * * * *